United States Patent [19]

Handschumacher et al.

[11] Patent Number: 5,047,512
[45] Date of Patent: Sep. 10, 1991

[54] IMMOBILIZED CYCLOPHILIN AND METHODS OF USING SUCH

[76] Inventors: Robert E. Handschumacher, 97 Great Harbor Rd., Guilford, Conn. 06437; Matthew W. Harding, 206 Goffe Ter., New Haven, Conn. 06511; David W. Speicher, 91 Fawn Dr., Cheshire, Conn. 06410

[21] Appl. No.: 65,395

[22] Filed: Jun. 23, 1987

Related U.S. Application Data

[62] Division of Ser. No. 730,776, May 3, 1985, Pat. No. 4,722,999.

[51] Int. Cl.$^5$ .................. C07K 17/12; G01N 33/566; G01N 33/53
[52] U.S. Cl. ..................................... 530/402; 530/408; 530/409; 530/411; 530/412; 530/413; 530/350; 530/810; 530/812; 530/813; 530/814; 530/815; 436/501; 436/503; 436/518; 436/528; 436/529; 436/530; 436/531; 436/532; 430/161; 430/824
[58] Field of Search ............... 530/402, 408, 409, 411, 530/412, 413, 350, 810, 812–815; 436/501, 161, 503, 518, 528–532, 824

[56] References Cited

PUBLICATIONS

Handschumacher et al., Science, 726, 1984, pp. 544–547.
Parukh et al., Cand EN, Aug. 1985, pp. 11–32.
Janson, Trends in Biotechnology 1984, vol. 2(2), pp. 31–38.

Primary Examiner—Garnette D. Draper
Attorney, Agent, or Firm—Ostrolenk, Faber, Gerb & Soffen

[57] ABSTRACT

Homogeneous cyclophilin, a soluble binding protein, having a specific binding activity of above 50 ug cyclosporin A per mg protein and a molecular weight of about 17,600 daltons, reversibly binds immunosuppressants or antibodies thereto such as cyclosporin or anti-cyclophilin. It is isolated from the cytosol of several different mammalian tissues and can be used in various diagnostic and purifications procedures.

15 Claims, 2 Drawing Sheets

Fig. 1

AMINO ACID SEQUENCE OF BOVINE CYCLOPHILIN

1
Val-Asn-Pro-Thr-Val-Phe-Phe-Asp-Ile-Ala-Val-Asp-Gly-Glu-Pro-Leu-Gly-Arg-Val-Ser-

Phe-Glu-Leu-Phe-Ala-Asp-Lys-Val-Pro-Lys-Thr-Ala-Glu-Asn-Phe-Arg-Ala-Leu-Ser-Thr-

Gly-Glu-Lys-Gly-Phe-Gly-Tyr-Lys-Gly-Ser-Cys-Phe-His-Arg-Ile-Ile-Pro-Gly-Phe-Met-

Cys-Gln-Gly-Gly-Asp-Phe-Thr-Arg-His-Asn-Gly-Thr-Gly-Gly-Lys-Ser-Ile-Try-Gly-Glu-
                                                    90
Lys-Phe-Asp-Asp-Glu-Asn-Phe-Ile-Leu-Lys-His-Thr-Gly-Pro-Gly-Ile-Leu-Ser-Met-Ala-

Asn-Ala-Gly-Pro-Asn-Thr-Asn-Gly-Ser-Gln-Phe-Phe-Ile-Cys-Thr-Ala-Lys-Thr-Glu-Trp-

Leu-Asp-Gly-Lys-His-Val-Val-Phe-Gly-Lys-Val-Lys-Glu-Gly-Met-Asn-Ile-Val-Glu-Ala-

Met-Glu-Arg-Phe-Gly-Ser-Arg-Asn-Gly-Lys-Thr-Ser-Lys-Lys-Ile-Thr-Ile-Ala-Asp-Cys-
163
Gly-Gln-Ile

Fig. 2

1. Gly-Phe-Gly-Tyr-Lys

2. Gly-Ser-Cys-Phe-His-Arg-Ile-Ile-Pro-Gly-Phe-Met-Cys-Gln-
   Gly-Gly-Asp-Phe-Thr-Arg-His-Asn-Gly-Thr-Gly-Gly-Lys

3. Ser-Ile-Tyr-Gly-Glu-Lys

4. Phe-Asp-Asp-Glu-Asn-Phe-Ile-Leu-Lys

5. His-Thr-Gly-Pro-Gly-Ile-Leu-Ser-Met-Ala-Asn-Ala-Gly-Pro-Asn-
   Thr-Asn-Gly-Ser-Gln-Phe-Phe-Ile-Cys-Thr-Ala-Lys

6. Thr-Glu-Trp-Leu-Asp-Gly-Lys

7. His-Val-Val-Phe-Gly-Lys

8. Val-Lys-Gln-Gly-Met-Asn-Ile-Val-Glu-Ala-Met-Glu-Arg-Phe-Gly-Ser-
   Arg-Asn-Gly-Lys

9. Lys-Ile-Thr-Ile-Ala-Asp-Cys-Gly-Gln-Ile

10. Val-Asn-Pro-Thr-Val-Phe-Phe-Asp-Ile-Ala-Val-Asp-Gly-Glu-Pro-Leu-Gly-
    Arg-Val-Ser-Phe-Glu-Leu-Phe-Ala-Asp-Lys-Val-Pro-Lys

11. Thr-Ala-Glu-Asn-Phe-Arg-Ala-Leu-Ser-Thr-Gly-Glu-Lys

IMMOBILIZED CYCLOPHILIN AND METHODS OF USING SUCH

This invention was made with government support under grant numbers GM 21714 and AM 27932 awarded by the National Institutes of Health. The government has certain rights in the invention.

This is a division of application Ser. No. 730,776, filed May 3, 1985 now U.S. Pat. No. 4,722,999.

BACKGROUND OF THE INVENTION

Cyclosporin A (CsA) is a cyclic undecapeptide of fungal origin and has potent immunosuppressant activity. It is widespreadly used in clinical transplantation for prevention of kidney, liver, pancreas and heart allograft rejection and for treating bone marrow recipients with acute graft v. host disease. It has also been suggested for use in the treatment of autoimmune diseases, malaria and schistosomiasis. Although CsA is not myelosuppressive, clinically important complications associated with CsA therapy include nephrotoxicity, hepatotoxicity and CNS disturbances.

CsA appears to act on the immune system by inhibiting the initial steps of interleukin-1 and antigen coactivation of T lymphocytes. It also blocks the production of interleukin-2 required for the differentation and proliferation of B cells and precursor cytolytic T cells. CsA also inhibits production of gamma interferon and lymphokines that mediate the delayed-type hypersensitivity and reactions and activate macrophages.

Merker et al, Cyclosporin Binding Components in BW5147 Lymphoblast and Normal Lymphoid Tissue, Transplantation Proceedings, Vol. XV, No. 4, Supplement 1, p. 2265 et seq. (December, 1983), reports the discovery of a high affinity binding component for CsA in the cytosol of normal T cells as well as a malignant cell line and the partial purification of the binding component from calf thymus as well as the malignant cell line. Purification was by molecular weight exclusion columns, isoelectric focusing and $(NH_4)_2SO_4$ precipitation to about 10% purity. The CsA-cytosol complex was indicated to have a molecular weight of 15,000–20,000.

It is the object of this invention to provide a new homogeneous cytosolic binding protein, cyclophilin, and affinity matrices containing cyclophilin and further to provide methods of using the cyclophilin as an affinity reagent in diagnostic and preparatory procedures.

This and other objects of the invention will become apparent to those skilled in the art from the following detailed description in which:

BRIEF DESCRIPTION OF THE DRAWINGS

FIG. 1 is the amino acid sequence of a bovine cyclophilin; and

FIG. 2 is eleven unique endoproteinase lysine C cleaved peptides of cyclophilin.

SUMMARY OF THE INVENTION

This invention relates to cyclophilin, purified to be homogeneous and having a specific binding activity of at least 50 ug CsA/mg protein and a molecular weight of about 17,600 daltons. It can be obtained from cytosol by molecular weight exclusion, Cibacron Blue chromatography, isoelectric focusing, and cationic chromatography. The cyclophilin, per se or immobilized, can be used as a specific binding partner to ligands for diagnostic, purification or investigatory procedures. A preferred immobilizing matrix is agarose having carboxy terminated $C_{12}$ spacer arms which form with the cyclophilin an affinity chromatography reagent.

DESCRIPTION OF THE INVENTION

The cytosolic CsA binding protein has now been successfully purified to homogeneity and is hereinafter termed cyclophilin. The amino acid composition and complete sequence of bovine thymocyte cyclophilin has been determined. It represents a new class of proteins unrelated to any known sequences in the protein sequence data base from the National Biomedical Research Foundation as of January, 1984.

Cyclophilin is of physiological importance because of the high specificity for binding active forms of the immunosuppressant CsA. An immobilized cyclophilin affinity matrix has been prepared that reversibly binds CsA in a 1:1 complex and can be used to detect cyclophilin-like proteins in tissue extracts as through a column containing the matrix. The matrix can also be used to detect cyclosporin-like substances by displacement of tritiated CsA ($^3$H-CsA). The matrix also provides a method to identify and/or quantify CsA in serum and other body fluids as well as detect cyclosporin-like cellular constituents which may be natural ligands. Still further, the matrix is useful in screening candidate chemical structures that, like cyclosporin, can have immunosuppressive activity and, therefore, is useful in the development of other classes of drugs that function through the action of this protein. The indirect demonstration of an interaction between cyclophilin and activities triggered by prolactin and calmodulin are examples of such a system. Additionally, the sera of from 20–30% of patients with systemic lupus erythematosis contain anti-cyclophilin antibodies so that cyclophilin functions as an antigen in diagnostic assays.

Cyclophilin is a homogeneous cytosolic binding protein which has a molecular weight of approximately 17,600 daltons. Bovine thymocyte cyclophilin contains 163 amino acid residues and identical or closely related forms can be obtained from the cytosol of various mammalian species. Typical procedures are set forth below. The bovine cyclophilin contains one tryptophan, two tyrosines, four methionines and is rich in lysine, phenylalanine and glycine. The complete amino acid sequence of a bovine cyclophilin is set forth in FIG. 1. It has been found that the N-terminal sequence (72 residues) of bovine and human cyclophilin is completely identical. Bovine cyclophilin has an isoelectric point of about 9.6 and exists in major and minor species which can be separated by weak cation exchange high pressure liquid chromatography. Human cyclophilin has isoelectric points of 7.4 and 9.1. The minor structural differences of the species do not affect CsA binding activity. The cyclophilin has been purified to the extent that it has CsA binding specific activity above 50 ug per mg of protein and preferably at least 65 ug/mg. Cyclophilin has also been found to have eleven unique endoproteinase lysine C cleaved peptides which are shown in FIG. 2.

Since cyclophilin has been purified to homogeneity, oligonucleotide probes can identify the cyclophilin gene thereby allowing cyclophilin to be produced by known recombinant DNA techniques.

A typical procedure for the purification of cyclophilin will next be described. In this procedure, CsA binding activity was measured by diluting test samples (10-90 ul) with assay buffer (20 mM $KH_2PO_4$, 5 mM 2-mercaptoethanol [hereinafter 2-ME]), pH 7.2 with a 0.02% sodium azide) containing 7.5% newborn calf serum. After addition of 10 ul $^3H$-CsA (50 ug/ml; 0.05 uCi/ml in 40% ethanol), tubes were agitated gently and 50 ul was applied to 1.8 ml Sephadex LH-20 (hydroxypropylated agarose) columns pre-equilibrated with assay buffer. The samples were then washed into the columns with 500 ul of assay buffer followed by an additional 500 ul to elute cyclophilin-CsA complexes. Elution fractions were diluted in 5.6 ml Liquiscint (a fluor-containing liquid to permit $\beta$-scintillation counting of $^3H$) and the binding activity quantified as equal to (cpm - background)÷(quench correction×$^3H$-CsA specific activity)×(volume of test sample).

Bovine thymus gland or human spleen cell tissue was homogenized for 45 seconds (1:4 weight:volume) in ice-cold 10 mM Tris, 150 mM KCl, 1 mM phenyl methyl sulfonyl fluoride, pH 7.2. 2-ME was added to a concentration of 5 mM and the tissue was homogenized for an additional 45 seconds. After centrifugation at 8,000× g for 20 minutes at 4° C., the supernatant was passed through glass wool and filtered through a 0.2 u Acroflux Capsule at 4°-10° C. As the filtrate was collected, the retentate volume was maintained by the addition of 10 mM Tris, 5 mM 2-ME, pH 7.2.

The clarified cytosol was filtered through a 5 square foot sulfone membrane with a 100,000 dalton exclusion limit in a Pellicon cassette system. Retentate was recirculated and the retentate volume maintained by addition of Tris buffer. The large filtrate volume was reduced by concentration to 500-1,000 ml with a 5 square foot 10,000 dalton exclusion membrane in the Pellicon cassette system. The filtrate and retentate samples were periodically tested to determine the efficiency and extent of CsA binding activity.

The CsA binding activity in the 10,000 dalton exclusion retentate was dialyzed against 10 mM potassium phosphate, 5 mM 2-ME, pH 7.2 at 4° C. and then adsorbed onto an affinity matrix (Dyematrix Blue A—Cibacron Blue dye bound through a $C_{12}$ spacer arm onto an agarose base matrix) column (5×30 cm) equilibrated with 10 mM potassium phosphate, 5 mM 2-ME, pH 7.2, also at 4° C. The column was washed with 500 ml of 10 mM potassium phosphate and then with 500 ml of 100 mM potassium phosphate, 5 mM 2-ME, pH 7.2. CsA binding activity was recovered by isocratic elution with 1000 ml of 300 mM potassium phosphate, 5 mM 2-ME, pH 7.2 at 3-6 ml/minute. The following Tables 1 and 2 summarize typical results to this point.

TABLE I

Purification of Bovine Thymocyte Cyclophilin

| Purification Step | Total Volume (ml) | Protein Conc. mg/ml | CsA Binding Activity (ug/ml) | (Total mg) | Specific Activity (mg CsA/ms Protein) | Recovery % |
|---|---|---|---|---|---|---|
| Cytosol Supernatant | 2880 | 9.50 | 3.91 | 20.00 | 0.41 | 100 |
| Acroflux Filtrate | 8100 | 0.91 | 1.86 | 15.38 | 2.04 | 76.7 |
| Pellicon 100 kd Filtrate | 24000 | 0.17 | 0.64 | 15.24 | 3.69 | 76.0 |
| Pellicon 10 kd Retentate | 1230 | 2.44 | 7.83 | 9.63 | 3.21 | 48.1 |
| Matrix Gel Blue A Chromatography | 895 | 0.86 | 9.62 | 8.61 | 11.91 | 43.0 |

TABLE 2

Purification of Human Splenocyte Cyclophilin

| Purification Step | Total Volume (ml) | Protein Conc. mg/ml | CsA Binding Activity (ug/ml) | (Total mg) | Specific Activity | Recovery % |
|---|---|---|---|---|---|---|
| Cytosol Supernatant | 750 | 5.71 | 0.80 | 600.0 | 0.14 | 100 |
| Acroflus Filtrate | 2750 | 0.41 | 0.18 | 495.0 | 0.44 | 82.5 |
| Pellicon 100 kd Filtrate | 9700 | 0.10 | 0.045 | 436.5 | 0.45 | 72.8 |
| Pellicon 10 kd Retentate | 275 | 3.52 | 1.55 | 426.3 | 0.44 | 71.0 |
| Matrix Gel Blue A | 250 | 0.08 | 1.74 | 417.6 | 22.3 | 69.6 |

It will be noted that the matrix blue dye affinity chromatography step provides a very significant increase in specific activity.

The matrix blue A fractions with CsA binding activity were pooled, dialyzed against 5 mM potassium phosphate, 5 mM 2-ME, pH 7.2. A maximum of 70 ug CsA binding activity was mixed in a 0-65% sucrose gradient containing 5 mM 2-ME and 1% ampholytes, pH 8-10.5 for bovine or pH 6-10.5 for human tissue extracts and electrofocused at 1600 V for 22 hours at 4° C. on a 110 ml preparative isoelectrofocusing column. The column was harvested at a flow rate of 1 ml/min. and the pH of each fraction was measured prior to titration with 1M potassium dihydrogen phosphate to pH 7.0.

Ampholytes were removed by pooling the CsA binding activity fractions, dialyzing against 1M potassium phosphate, 5 mM 2-ME, pH 7.2 and absorbing to a phenyl Sepharose column (2.5×30 cm) at 4° C. pre-equilibrated with 1M potassium phosphate, 5 mM 2-ME, pH 7.2. The column was washed with 100 ml of 1M potassium phosphate and the CsA binding activity eluted with 500 ml of 10 mM potassium phosphate, 5 mM 2-ME, pH 7.2.

The isoforms of bovine cyclophilin were separated by weak cation exchange high pressure liquid chromatography. The CsA binding activity recovered after phenyl Sepharose chromatography was dialyzed against 5 mM potassium phosphate, 5 mM 2-ME, pH 7.2. Samples were injected onto a weak cation exchange HPLC column (Synchropak CM300:4.1×250 mM; pore size 300 Å) pre-equilibrated with 5 mM potassium phosphate, 5 mM 2-ME, pH 7.2. The isoforms were eluted at 1 ml/min with a concave gradient (5 mM potassium phosphate, pH 7.2 to 175 mM NaCl, 5 mM potassium phosphate, pH 7.2) generated with a gradient programmer. Milligram quantities of the bovine cyclophilin isoforms were obtained by automating injection, gradient elution and collection. The major and minor isoforms of cyclophilin have CsA binding specific activities of 77 and 67 ug per mg of protein, respectively. This corresponds to about one mole of CsA bound per mole of cyclophilin species. The disassociation constant is about $2 \times 10^{-7}$M.

The CsA binding activity of cyclophilin is sulfhydryl dependent, unstable at 56° C. and at pH 4 or 9.5, and sensitive to proteases, i.e. trypsin.

The specificity of cyclophilin for binding CsA and several natural and synthetic derivatives of CsA was examined with respect to the ligand's ability to enhance the intrinsic fluorescence of tryptophan in cyclophilin. This was quantified by measurement of fluorescence after addition of CsA or analogs (0.25 or 1.0 ug/ml) to 2.5 ml of 5 mM $KH_2PO_4$ buffer (pH 7.2) containing 5 ug/ml cyclophilin and 5 mM 2-ME. As a measure of hydrophobicity, the retention of analog relative to CsA was determined on a uBondapak phenyl column (3.9×300 mM; 100 A pore size) monitored at 210 nm with isocratic elution with 60% acetonitrile at 1 ml/min. The results are shown in the following table.

TABLE 3

| Compound | Immuno-suppressive activity in mixed lymphocyte reaction | Cyclophilin affinity 0.25 ug/ml | Cyclophilin affinity 1.0 ug/ml | Retention time of analog relative to CsA |
| --- | --- | --- | --- | --- |
| CsA | +++ | 0.34 | 0.90 | 1.00 |
| CsC | +++ | 0.31 | 0.69 | 0.70 |
| Dihydro-CsC | +++ | 0.33 | 0.70 | 0.79 |
| CsC ester | +++ | 0.00 | 0.04 | 1.40 |
| CsG | ++ | 0.30 | 0.87 | 1.14 |
| Dihydro-CsD | + | 0.19 | 0.72 | 1.28 |
| 8-Acido-dihydro-CsA | + | 0.12 | 0.53 | 1.00 |
| CsD | ± | 0.21 | 0.69 | 1.20 |
| CsH | − | −0.01 | 0.02 | 0.98 |
| O-Acetyl-CsA | − | −0.02 | −0.03 | 1.69 |

Only those compounds which inhibited mixed lymphocyte reactions were capable of binding to cyclophilin. An exception, however, was an ester of cyclosporin C that may be metabolized by macrophage nonspecific esterase in the mixed lymphocyte reaction to yield free CsC. Further evidence for the specicifity of cyclophilin for CsA is apparent in the lack of correlation between the hydrophobic nature of cyclosporin derivatives, as determined by hydrophobic interaction HPLC and their affinity of cyclophilin.

Since cyclophilin has an affinity for immunusuppressants such as CsA and its active analogs, and anticyclophilin antibodies, it or certain active chemical and/or natural derivatives thereof including subfragments of the whole protein can be used as a specific binding partner for these ligands in numerous receptor binding procedures known in the art. Similarly, it can be used to purify the ligand from a composition containing ligand. For example, the cyclophilin can be used for purifying CsA or related structures from a yeast fermentation broth in which the CsA is produced. Further, it can be used to select compounds which bind to cyclophilin as a screening test for identifying new immunosuppressant drugs. In these various procedures, it is preferred, although not required, to immobilize the cyclophilin. This can be accomplished by any procedure known in the art. A particularly useful immobilizing matrix is agarose having carboxy terminated $C_{12}$ spacer arm esterfied to N-hydroxysuccinimide. This matrix is commercially available under the name Affigel-10 (Biorad). The immobilized cyclophilin is prepared by effecting a transamination with the N-hydroxysuccinimide being split off and the cyclophilin replacing it. The binding of the cyclophilin to this matrix can result in a marked stabilization of the bound activity through a three-dimensional stabilization achieved by multiple bonds through the ϵ-amino groups of lysine. The remarkable stability can be demonstrated by exposure to 8M urea for more than one hour as well as to 30% acetonitrile; unbound cyclophilin in solution with 8M urea experiences at least 60% irreversible loss of CsA binding activity after dialysis to remove urea and complete loss of activity after a 10 minute exposure to 30% acetonitrile.

The immobilized cyclophilin can be used as an affinity matrix prepared as follows:

A 1 ml column was prepared with the preferred immobilized cyclophilin in a Pasteur pipette and equilibrated at 0.1 ml/min with a 2 ug/ml solution of $^3$H-CsA ($2.2 \times 10^3$ cpm/ug) in sodium phosphate buffer (20 mM, pH 7.2) containing 5 mM 2-ME and 0.02% sodium azide. It required a large volume of this solution of $^3$H-CsA to equilibrate entering and exiting CsA solutions as compared to a column prepared with an equivalent amount of cytochrome C in place of the cyclophilin. The column was washed with 5 ml of the phosphate buffer, at 0.1 ml/min, and under these conditions had a background elution rate of 200 cpm/ml. Complete disassociation of $^3$H-CsA from the column was achieved by 9 ml of 8M urea and revealed a binding capacity of 7.2 ug of cyclosporin/ml of matrix or 4.7 ug/mg of bound protein. A subsequent preparation of the column at pH 9.0 had a binding capacity of 11.5 mg CsA/ml matrix or 11.5 ug CsA/mg protein. Two months later, no change in the specific activity was observed. In comparison, the comparable cytochrome C column retained less than 0.5 ug of CsA during the equilibration phase as evidenced by the volume required to equilibrate the entering and exiting concentration of CsA. Furthermore, elution with 8M urea failed to displace detectable amounts of $^3$H-CsA. Potassium isothiocyanate (0.1M), a strong chaotropic salt, and 50% ethylene glycol in the sodium phosphate buffer failed to elute CsA from the cyclophilin-containing column and it was noted that the preferred column was stable for 6 months stored as the CsA complex at 4° C. and in the sodium phosphate buffer. The dissociation constant of the cyclophilin-CsA complex appears to be essentially the same as that of cyclophilin in solution.

The preferred immobilized cyclophilin has been used as a high pressure liquid chromatography detector for cyclosporin binding proteins as they elute from either a commercially available HPLC molecular sieve (TSk-2000) or weak cation resin (CM-300). The isocratic buffer used in the HPLC column was sodium phosphate (0.2M, pH 7.2) containing 5 mM 2-ME. Two ml of the immobilized cyclophilin was packed into a standard Pasteur capillary pipette and saturated with $^3$H-CsA ($2.2 \times 10^3$ cpm/ug). The column was placed on line immediately after an ultraviolet detector and the column eluted at 0.5 ml/min with the 0.2M phosphate buffer. After the equilibration with 20 ml of the running buffer, radioactivity in the effluent was approximately 20 cpm/ml above background. In the presence of normal cyclosporin binding activity ($\leq 0.2$ ug CsA/mg protein; $\leq 20$ mg/ml; $\leq 0.5$ ml injected volume) in cell extracts, it was possible to pass at least 360 ml of equilibrating running buffer (at 45 ml per analysis) through the column without significantly depleting the response of the 2 ml indicator column. The effluent was collected directly into plastic minivials in 0.5 ml fractions and counted on a liquid scintillation spectrometer in 5.6 ml of Liquiscint. Extracts of murine brain, Aplysia gonads and highly purified cyclophilin from calf thymus gave a response that had a high resolution, an excellent signal to noise ratio, and was proportional to the CsA binding activity applied.

The preferred immobilized cyclophilin can also be used for the determination of the concentration of endogeneous cyclosporin and its metabolites from physiological fluids and tissue extracts. In one procedure, 100 ul of rat bile from hourly bile fractions collected after intraveneous administration of 20 mg $^3$H-CsA/kg ($2.5 \times 10^6$ cpm) was passed through a 2 ml column of the preferred immobilized cyclophilin having no bound CsA. This bile contained 180 ug/ml of cyclosporin and its metabolites based on radioactivity. In the bile sample obtained one hour after the intraveneous injection of cyclosporin, approximately 50% of the radioactivity was present as intact cyclosporin and the remainder was largely a major metabolite. Eighty percent of the radioactivity was retained by the immobilized cyclophilin. A bile sample obtained 7 hours after CsA injection contained virtually no cyclosporin and for not only the initial major metabolites but other radioactive derivatives of cyclosporin, a similar retention was observed. This suggests that the metabolites retained affinity for the cyclophilin.

The cyclophilin can further be used in diagnostic assays. In one procedure, an ELISA was conducted with sera from patients with systemic lupus erythematosis. The bottoms of the wells of a 96 well microtiter assay plate were coated with cyclophilin and the nonspecific binding sites were blocked with human cord serum. The sera from individuals suspected of having systemic lupus erythematosis as well as control patients were added to the wells, incubated and then the wells were washed. Goat anti-human antibodies which have been conjugated with an enzyme were applied to the assay plate wells and incubated for a time sufficient to permit any binding between the antibodies. Thereafter, the visualization of bound anticyclophilin antibodies was effected in the conventional fashion by adding a substrate for the enzyme which reacts in the presence of the enzyme to form a colored product.

Various changes and modifications can be made in the products and processes of the present invention without departing from the spirit and scope thereof.

The various embodiments which have been set forth herein were for the purpose of further illustrating the invention but were not intended to limit it.

What is claimed is:

1. Cyclophilin, a homogeneous cytosolic binding protein having a specific binding activity above 50 ug cyclosporin A per mg of protein bound and a molecular weight of about 17,600 daltons, immobilized on a support.

2. The immobilized cyclophilin of claim 1 in which said cyclophilin has a specific binding activity above 65 ug cyclosporin A per mg of protein bound and said support comprises agarose having a carboxy terminated 12 carbon atom spacer arm.

3. In a method of determining the presence or quantity of a ligand in a sample by effecting a specific binding assay during which the sample is combined with a specific binding partner of the ligand under binding conditions, the improvement which comprises the specific binding partner being cyclophilin, a homogeneous cytosolic binding protein having a specific binding activity above 50 ug cyclosporin A per mg of protein bound and a molecular weight of about 17,600 daltons, and said ligand being a cyclophilin receptor.

4. The method of claim 3, wherein said cyclophilin is immobilized.

5. The method of claim 4, in which said cyclophilin has a specific binding activity above 65 ug cyclosporin A per mg of protein bound immobilized on agarose having a carboxy terminated 12 carbon atom spacer arm.

6. The method of claim 5, wherein said sample is sera of a patient suspected of having systemic lupus erythamatosis.

7. The method of claim 6, further comprising the steps of separating said sera and said cyclophilin and thereafter contacting said cyclophilin with labeled systemic lupus erythamatosis antibodies.

8. The method of claim 3 used to purify the endogenous ligand for cyclophilin from a sample containing said ligand.

9. The method of claim 3 which is used to purify cyclosporin A.

10. The method of claim 5, wherein said immobilized cyclophilin has been equilibrated with tritiated cyclosporin A, whereby the ligands capable of displacing the tritated cyclosporin A are detected.

11. The method of claim 4, wherein said immobilized cyclophilin has been equilibrated with tritiated cyclosporin A, whereby the ligands capable of displacing the tritated cyclosporin A are detected.

12. The method of claim 3, wherein said ligand is an immunosuppressant or anti-cyclophilin antibodies.

13. The method of claim 12, wherein the immunosuppressant is cyclosporin A or an analog thereof.

14. In a method of isolating an receptor from its environment by contact with immunoadsorbent, the improvement which comprises employing as immunoadsorbent, cyclophilin, a homogeneous cytosolic binding protein having a specific binding activity above 50 ug cyclosporin A per mg of protein bound and a molecular weight of about 17,600 daltons and wherein said receptor is adsorbable to said cyclophilin.

15. The method of claim 20 wherein said cyclophilin is immobilized.

* * * * *